US009211255B2

United States Patent
Kim (10) Patent No.: US 9,211,255 B2
(45) Date of Patent: Dec. 15, 2015

(54) FACE SUPPORT HAVING A DRUG CARRIER

(75) Inventor: Hi Gu Kim, Gwangju (KR)

(73) Assignees: Hi Gu Kim, Gwangju (KR); Spacepower Co., LTD, Gwangju (KR)

( * ) Notice: Subject to any disclaimer, the term of this patent is extended or adjusted under 35 U.S.C. 154(b) by 821 days.

(21) Appl. No.: 13/503,451

(22) PCT Filed: Oct. 25, 2010

(86) PCT No.: PCT/KR2010/007342
§ 371 (c)(1),
(2), (4) Date: Jul. 6, 2012

(87) PCT Pub. No.: WO2011/049419
PCT Pub. Date: Apr. 28, 2011

(65) Prior Publication Data
US 2012/0323064 A1 Dec. 20, 2012

(30) Foreign Application Priority Data
Oct. 23, 2009 (KR) .................. 10-2009-0101423

(51) Int. Cl.
*A61M 31/00* (2006.01)
*A61K 9/00* (2006.01)
(Continued)

(52) U.S. Cl.
CPC .............. *A61K 9/0048* (2013.01); *A61F 9/0026* (2013.01); *A61K 8/0204* (2013.01);
(Continued)

(58) Field of Classification Search
CPC ............. A61F 2007/0004; A61F 9/008; A61F 9/0026; A61F 9/007; A61F 9/04; A61K 9/0048; A61K 8/0204; A61K 8/97; A61K 2800/81; A61B 18/203; A61B 2018/0047; A61N 2005/0648; A61N 2005/0659; A61N 2005/0652; A61N 2005/0654; A61N 2005/0661; A61Q 19/08
See application file for complete search history.

(56) References Cited

U.S. PATENT DOCUMENTS

2003/0056281 A1    3/2003  Hasegawa
2004/0147984 A1*   7/2004  Altshuler et al. ............... 607/88
2006/0235494 A1*  10/2006  Vanderschuit .................. 607/89

FOREIGN PATENT DOCUMENTS

JP    2003-093431 A   4/2003
KR   2007-0053408 A   5/2007
(Continued)

OTHER PUBLICATIONS

International Search Report for Application No. PCT/KR/2010/007342 dated Jul. 27, 2011.

*Primary Examiner* — Bhisma Mehta
*Assistant Examiner* — Bradley Osinski
(74) *Attorney, Agent, or Firm* — Alston & Bird LLP (57) ABSTRACT

The present disclosure relates to a face support that has a built-in drug carrier containing medicinal ingredients for protecting eyes from diseases and reducing wrinkles around the eyes. The face support having a drug carrier according to the present disclosure is designed to cover a facial area around the eyes and comprises: a housing with a predetermined installation space defined therein and a plurality of vent holes formed in one side in the proximity of the globe of the eye when the face support is worn, the vent holes serving to communicate the installation space with the outside; a main body having a fixing member for fixing the housing to the face of a user; and a drug carrier installed inside the main body and containing medicinal ingredients useful for protecting the eyes from diseases and relieving eye fatigue. The drug carrier comprises a medicinal herb layer containing the medicinal ingredients to enable transdermal delivery of the medicinal ingredients. As the medicinal ingredients for relieving eye fatigue and protecting the eyes from diseases directly penetrate through the skin or a mucosa, the face support having a drug carrier according to the present disclosure is very advantageous in that it is convenient to use and is excellent in relieving fatigue and reducing wrinkles around the eyes.

9 Claims, 4 Drawing Sheets

(51) Int. Cl.
 *A61Q 19/08* (2006.01)
 *A61K 8/97* (2006.01)
 *A61K 8/02* (2006.01)
 *A61F 9/00* (2006.01)
 *A61B 18/20* (2006.01)
 *A61B 18/00* (2006.01)
 *A61N 5/06* (2006.01)

(52) U.S. Cl.
 CPC ............... *A61K 8/97* (2013.01); *A61Q 19/08* (2013.01); *A61B 18/203* (2013.01); *A61B 2018/0047* (2013.01); *A61B 2018/00452* (2013.01); *A61K 2800/81* (2013.01); *A61N 2005/0648* (2013.01); *A61N 2005/0652* (2013.01); *A61N 2005/0654* (2013.01); *A61N 2005/0659* (2013.01); *A61N 2005/0661* (2013.01)

(56) References Cited

FOREIGN PATENT DOCUMENTS

| KR | 10-0831151 B1 | 5/2008 |
| KR | 2009-0050656 A | 5/2009 |
| WO | WO 2008/153281 A1 | 12/2008 |

\* cited by examiner

FACE SUPPORT HAVING A DRUG CARRIER

CROSS-REFERENCE TO RELATED APPLICATION

This application is a national stage application filed under 35 U.S.C. 371 of International Application No. PCT/KR2010/007342, filed Oct. 25, 2010, which claims priority from Korean Patent Application No. 10-2009-0101423, filed Oct. 23, 2009, each of which is incorporated by reference herein in its entirety.

TECHNICAL FIELD

The present disclosure relates to a support worn on the face having a built-in drug carrier. More particularly, it relates to a support worn on the face which has a built-in drug carrier containing medicinal ingredients for protecting eyes from diseases and reducing wrinkles around the eyes.

BACKGROUND ART

Human eyes are located in the front of the head, inside a pair of orbital sockets, and are protected by upper and lower eyelids. The eye consists of the globe, the optic nerve and appendages (the eyelids, the conjunctiva, the lacrimal apparatus and the eye muscles).

Recently, as many office works are performed with computers, people spend a lot of time staring at computer monitors. Also, with increased TV and 3D video watching time, fatigue to the eyes is increasing ever.

Although it is best to close eyes and take a rest to relive the eye fatigue, people find it difficult to do so due to lack of time. Thus, they usually resort to oral medicines helpful in reliving eye fatigue, including vitamin E.

However, the effect of the orally administered drug decreases as the active ingredient passes through the liver and the fatigue-relieving effect is only temporary.

Wrinkles may increase rapidly around the eyes due to undue stress and exposure to UV. Although many women use functional cosmetics or receive surgery to reduce the wrinkles around the eyes, the effect of the cosmetics is insufficient and the surgery costs a lot.

DISCLOSURE

Technical Problem

The present disclosure is directed to providing a support worn on the face having a built-in drug carrier containing medicinal ingredients for protecting eyes from diseases and reducing wrinkles around the eyes.

Technical Solution

In one general aspect, the present disclosure provides a support worn on the face having a built-in drug carrier comprising: a housing with a predetermined installation space defined therein and a plurality of vent holes formed in one side in the proximity of the globe of the eye when the support worn on the face is worn, the vent holes serving to communicate the installation space with the outside; a main body having a fixing member for fixing the housing to the face of a user; and a drug carrier installed inside the main body and containing medicinal ingredients useful for protecting the eyes from diseases and relieving eye fatigue, wherein the drug carrier comprises a medicinal herb layer containing the medicinal ingredients to enable transdermal delivery of the medicinal ingredients.

The drug carrier may further comprise a medicinal ingredient delivery activating means for activating the transdermal delivery of the medicinal ingredients contained in the medicinal herb layer. The medicinal ingredient delivery activating means may comprise at least one selected from a light emitting means emitting UV or IR light, a magnet generating a magnetic field and a low frequency generator, which are installed on a substrate provided inside the housing to support the medicinal herb layer.

The housing may be equipped with an auxiliary LED light-emitting module irradiating light with wavelength of 430-670 nm toward the face of the user in order to reduce wrinkles around the eyes. And, a light guide plate contacting with the skin around the eyes may be formed inside the housing and a light-emitting diode may be installed at one side of the light guide plate so as to irradiate light with wavelength of 430-670 nm through the light guide plate.

The medicinal herb layer may comprise a pad formed by pulverizing or extracting at least one medicinal herb selected from duckweed, semiaquilegia, grape, yellow bean, hibisci cortex, citri pericarpium, grape root, lettuce, lettuce seed, pea flower, ginko nut, rugosa rose, sunflower, sunflower root, rose of Sharon, equiseti herba, ginkgonis germen, glycinis testa, ginseng nodus, spinaciae herba, mori cortex, mori fructus, mori folium, persicae fructus immaturus, pruni lignum, pruni resina, pruni radix, pruni folium, pruni ramulus, pruni semen, pruni flos, mori favilla, motherwort, lonicerae folium, lonicerae flos, porpyrae siccus, pruni caulis, persicae calyx, petasiteae rhizoma, colocasiae rhizoma, *Colocasia esculenta* tuber, *Colocasia esculenta* folium, armeniacae semen, ricini semen, glycinis semen ptisanari, whole plant of *Trichosanthes cucumeroides*, pini pollen, fici fructus, brassicae herba, eriobotryae fructus, pini cortex, pini polium, terebinthinae oleum, hirundinis nidus, fucus cum caesalpiniae, fucus cum carthami, *Trichosanthes cucumeroides* semen, melo pediculus, raphani radix, glycine semen nigrae, tuberous root of *Trichosanthes cucumeroides, Trichosanthes cucumeroides* radix, juniperi favilla, ricini folium, carthami flos, carthami novella, trigonellae semen, verbenae herba, carthami semen, curcumae radix, *Curcuma longa* rhizoma, apis nidus, mali fructus, *Angelica sinensis* radix, honey, ginseng, acanthopanacis cortex, hordei fructus germinatus, wild honey, auriculariae polyporus, phragmitis folium, toonae folium, toonae radicis cortex, massa medicata fermentata, phragmitis rhizoma, phragmitis favilla, *Allium fistulosum*, capsellae semen, capsellae herba, coprini herba, *Citrus unshiu* immature peel, *Colocasia esculenta* rhizoma, amaranthi semen, lycii radicis cortex, cyperi rhizoma, perillae folium, allii bulbus, sanguisorbae radix, cnidii rhizoma, *Acorus calamus* rhizoma, papaveris fructus pericarpium, portulacea herba, foeniculi fructus, raphani semen, cnidii surculus, cassiae folium, ixertis herba, lasiosphaera seu calvatia, sacchari tuber, lycii fructus, asparagi radix, liriopes radix, rehmanniae radix, rehmanniae radix preparata, white ginseng, mint, tangerine, sweet potato, poria, dioscoreae rhizoma, achyranthis radix, dendrobii herba, cassiae semen, chrysanthemum, cuscutae semen, aurantii fructus pericarpium, gazellae cornu, saposhnikovia radix, celosiae semen, schizandrae fructus, glycyrrhizae radix, coptidis rhizoma, tribuli fructus, ligustici rhizoma, osterici radix, viticis fructus, glycyrrhizae radix preparata, gypsum, scutellariae radix, forsythiae fructus, moutan cortex, alismatis rhizoma, corni fructus, marigold, angelicae gigantis radix, hirudonis caro, cicadae periostracum, bupleuri radix, cimicifugae rhizoma, clematidis radix, anemarrhenae rhizoma, atractylodis rhizoma, scrophulariae radix, *Angelica pubescens* radix, sophorae radix, thujae resina, *Polygonum mulliflorum* radix, astragali radix, schizonepetae spica, fingered citron, banana, mushroom, blueberry, green coffee berry, green tea, kale, carrot, spinach, pumpkin and broccoli. The medicinal herb layer may further comprise at least one medicinal herb selected from lemon, orange, cherry, pomegranate, strawberry, rose, lilac, acacia, freesia, lily, lavender, mint, jasmine, mugwort, rosemary, pine, flavonoid, fir, coffee, fingered citron, chamomile, cypress, geranium, juniper, roseclary, sage, lime, neroli, sandalwood bergamot, eucalyptus, lime neroli, peppermint, ylang-ylang, patchouli, myrrh, frankincense, cedarwood, sandalwood, which is extracted and encapsulated to form the medicinal herb layer.

The fixing member may be formed such that it extends backwards from the housing and its rear ends are placed over the ears of the user, and the housing or the fixing member may be equipped with a magnet member capable of stimulating at least one part selected from the Taiyang acupoints corresponding to the temples of the user, the Qiuhou and Chengqi acupoints below the eyes, the Wangu and Fengchi acupoints at the back of the head, and the ridge of the nose.

View holes may be formed in the housing so that the user can see ahead while wearing the support worn on the face. A pair of the view holes may be formed in the housing, in front of the right and left eyes, and the housing may be further equipped with two polarizing lenses of different polarizing directions, each of which is installed to cover each of the view holes.

Advantageous Effects

The support worn on the face having a built-in drug carrier according to the present disclosure is very advantageous in that it is convenient to use and is excellent in relieving fatigue and reducing wrinkles around the eyes since the medicinal ingredients for relieving eye fatigue and protecting the eyes from diseases directly penetrate through the skin or a mucosa.

Further, since the support worn on the face having a built-in drug carrier provides good sight, the user's eyes can be protected by administering drugs at any time in daily life to relieve eye fatigue. In addition, blood circulation can be promoted by stimulating the acupoints on the face or at the back of the head.

When polarizing lenses or liquid crystal cells are attached to the main body, the user can watch 3D video with minimized eye fatigue.

BEST MODE

Hereinafter, a support worn on the face having a built-in drug carrier according to the present disclosure will be described in detail with reference to accompanying drawings.

Figure 1:
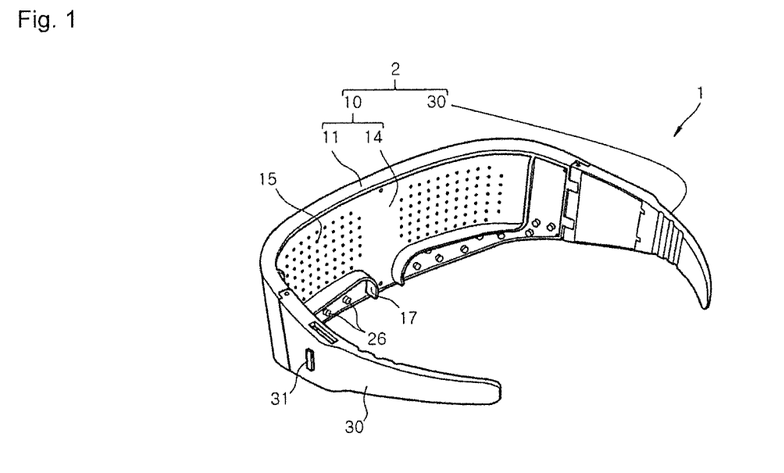
FIG. 1 is a perspective view of a support worn on the face having a built-in drug carrier according to a first embodiment the present disclosure.
Figure 2:
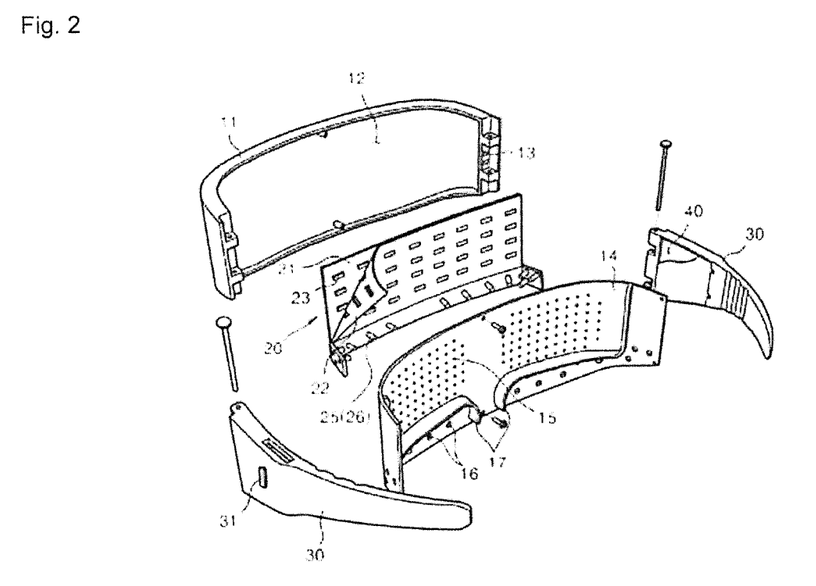
FIG. 2 is an exploded perspective view of FIG. 1.
Figure 3:
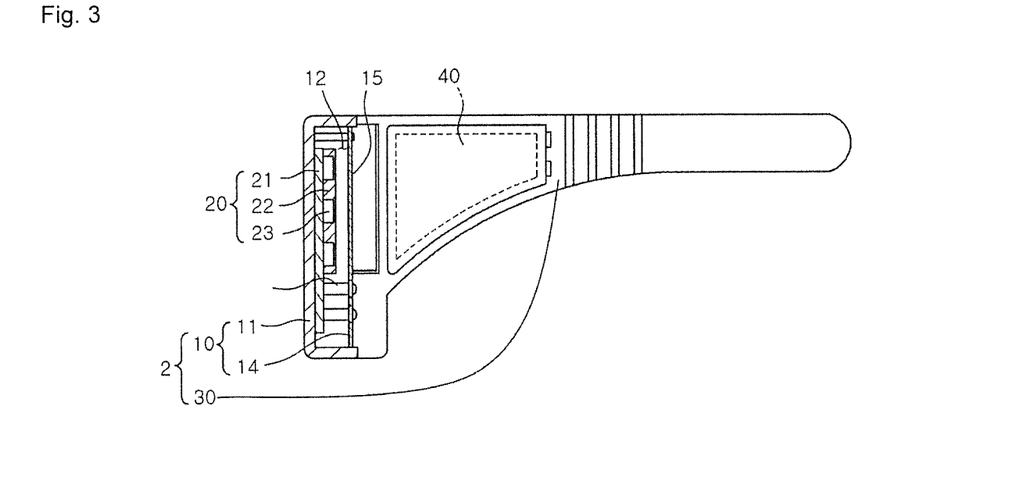
FIG. 3 is a cross-sectional view of the housing of FIG. 1.

FIGS. 1-3 show a support worn on the face 1 according to an exemplary embodiment of the present disclosure.

Referring to the figures, the support worn on the face 1 comprises a main body 2, a drug carrier 20 installed inside the main body 2, and a battery 40 supplying power to the drug carrier 20.

The main body 2 is equipped with a housing 10 and a fixing member 30 for fixing the housing 10 to the face of a user.

The housing 10 comprises an outer case 11 and an inner case 14 which are coupled with each other. It provides an installation space 12 in which the drug carrier 20 is installed and covers eyes and the face around the eyes.

At each end of the outer case 11, a first power supply terminal 13 is provided to receive power supplied from the battery 40. The power is supplied to the drug carrier 20 via an electric wire connected to the first power supply terminal 13.

The inner case 14 is coupled with the outer case 11 and contacts the face of the user.

The inner case 14 has a plurality of vent holes 15 so that medicinal ingredients may be released from the drug carrier 20 installed in the installation space 12. Below the inner case 14, a plurality of light irradiation holes 16 are formed such that an auxiliary light-emitting diode of an auxiliary LED light-emitting module 25 may be exposed toward the face of the user.

On the outer surface of the inner case 14 contacting with the face of the user, shielding plates 17 protruding toward the face of the user are formed between the vent holes 15 and the light irradiation holes 16. The shielding plates 17 are provided to shield the light emitted from the auxiliary LED light-emitting module 25 to be irradiated to the eyes of the user. The shielding plates 17 are formed to extend from the middle bottom portion of the inner case 14 toward both ends of the inner case 14.

The drug carrier 20 comprises a substrate 21, a medicinal herb layer 22 mounted on the substrate 21, and a plurality of light-emitting lamps 23 installed on the substrate 21 and irradiating UV or IR light for activating transdermal delivery of the medicinal ingredients.

Although not shown in the figures, a plurality of mounting units are formed on the substrate 21 so that the light-emitting lamps 23 can be mounted. Each of the mounting units is electrically connected such that power can be supplied to the light-emitting lamps 23. Hence, when power is supplied to the substrate 21 via the electric wire, all the light-emitting lamps 23 mounted on the mounting units emit light.

Specifically, the light-emitting lamp 23 may employ a light-emitting diode which consumes less power. Due to the light irradiated from the light-emitting lamp 23 and the heat generated from the light-emitting lamp 23, the medicinal ingredients contained in the medicinal herb layer 22 may diffuse actively.

Although the light-emitting lamp is used in this embodiment as a medicinal ingredient delivery activating means for activating the delivery of the medicinal ingredients, a magnet generating a magnetic field or a low frequency generator generating low-frequency waves may also be used as the medicinal ingredient delivery activating means.

The medicinal herb layer 22 is installed on the substrate 21 and contains the medicinal ingredients.

The medicinal herb layer 22 is prepared into the form of a pad. The medicinal ingredients contained in the medicinal herb layer 22 are those useful in protecting eyes from diseases and relieving eye fatigue, such as lutein, zeaxanthin, melatonin, β-carotene, L-carnitine, astaxanthin, α-lipoic acid), carnosine, epigallocatechin gallate, acetyl-L-carnitine, curcumin, anthocyanin, drevogenin D, sulforaphane, carotenoids, folic acid, vitamin A, vitamin B, vitamin C, tetramethylpyrazine, fisetin, cannabinoids and vitamin E.

The medicinal herb layer 22 may contain at least one of the above-described medicinal ingredients.

The above-described medicinal ingredients may be obtained by pulverizing or extracting natural medicinal herbs.

For example, lutein is contained in duckweed, semiaquilegia, grape, yellow bean, hibisci cortex, citri pericarpium, grape root, lettuce, lettuce seed, pea flower, ginko nut, rugosa rose, sunflower, sunflower root, rose of Sharon, equiseti herba, ginkgonis germen, glycinis testa, ginseng nodus and spinaciae herba, and zeaxanthin may be extracted from mori cortex, mori fructus, mori folium, persicae fructus immaturus, pruni lignum, pruni resina, pruni radix, pruni folium, pruni ramulus, pruni semen, pruni flos, citri pericarpium, ginkgonis germen, mori favilla, motherwort, lonicerae folium, lonicerae flos, equiseti herba, porpyrae siccus, pruni caulis, persicae calyx, spinaciae herba or grape.

Melatonin may be extracted from petasiteae rhizoma, colocasiae rhizoma, *Colocasia esculenta* tuber or *Colocasia esculenta* folium, and β-carotene may be extracted from armeniacae semen, ricini semen, glycinis semen ptisanari, citri pericarpium, whole plant of *Trichosanthes cucumeroides*, hibisci cortex, rose of Sharon, pini pollen, fici fructus, ginkgonis germen, brassicae herba, eriobotryae fructus, pini cortex, pini polium, terebinthinae oleum, brassicae herba, glycinis testa, hirundinis nidus, fucus cum caesalpiniae, fucus cum carthami, lettuce, lettuce seed, pea flower, *Trichosanthes cucumeroides* semen, *Colocasia esculenta* tuber, porpyrae siccus, melo pediculus, persicae fructus immaturus, raphani radix, semiaquilegia, sunflower, sunflower root, eriobotryae folium, pruni lignum, pruni resina, pruni radix, pruni caulis, pruni folium, pruni ramulus, pruni semen, pruni flos, glycine semen nigrae, spinaciae herba, tuberous root of *Trichosanthes cucumeroides, Trichosanthes cucumeroides* radix, juniperi favilla, *Colocasia esculenta* folium, ginko nut, persicae calyx, ricini folium, carthami flos, carthami novella, rugosa rose, lonicerae folium, lonicerae flos, trigonellae semen, verbenae herba, equiseti herba, carthami semen or yellow bean.

Curcumin may be extracted from curcumae radix or *Curcuma longa* rhizoma, folic acid may be extracted from apis nidus, mali fructus, *Angelica sinensis* radix, honey, ginseng nodus or ginseng, vitamin B$_1$ may be extracted from acanthopanacis cortex, hordei fructus germinatus, wild honey, auriculariae polyporus, phragmitis folium, toonae folium, toonae radicis cortex, massa medicata fermentata, ricini folium, phragmitis rhizoma, porpyrae siccus, phragmitis favilla or ricini semen, and vitamin C may be extracted from *Allium fistulosum*, capsellae semen, capsellae herba, coprini herba, *Citrus unshiu* immature peel, toonae folium, *Colocasia esculenta* rhizoma, amaranthi semen, lycii radicis cortex, cyperi rhizoma, trigonellae semen, perillae folium, allii bulbus, sanguisorbae radix, cnidii rhizoma, *Acorus calamus* rhizoma, papaveris fructus pericarpium, portulacea herba, raphani radix, foeniculi fructus, raphani semen, cnidii surculus, porpyrae siccus, cassiae folium, ixertis herba, lasiosphaera seu calvatia, sacchari tuber or lycii fructus. The medicinal ingredients useful for protecting eyes from diseases and relieving eye fatigue may be extracted from these medicinal herbs.

In addition, the medicinal herb layer 22 containing the medicinal ingredients may be prepared by pulverizing or extracting at least one medicinal herb selected from asparagi radix, liriopes radix, rehmanniae radix, rehmanniae radix preparata, white ginseng, mint, tangerine, sweet potato, poria, dioscoreae rhizoma, lycii fructus, achyranthis radix, dendrobii herba, cassiae semen, armeniacae semen, chrysanthemum, cuscutae semen, aurantii fructus pericarpium, gazellae cornu, saposhnikovia radix, celosiae semen, schizandrae fructus, glycyrrhizae radix, coptidis rhizoma, tribuli fructus, ligustici rhizoma, chrysanthemum, equiseti herba, osterici radix, viticis fructus, glycyrrhizae radix preparata, gypsum, scutellariae radix, forsythiae fructus, moutan cortex, alismatis rhizoma, corni fructus, marigold, tribuli fructus, angelicae gigantis radix, hirudonis caro, cicadae periostracum, bupleuri radix, cimicifugae rhizoma, ginseng, clematidis radix, anemarrhenae rhizoma, citri pericarpium, atractylodis rhizoma, scrophulariae radix, *Angelica pubescens* radix, carthami semen, acanthopanacis cortex, sophorae radix, thujae resina, *Polygonum multiflorum* radix, astragali radix, schizonepetae spica, fingered citron, banana, mushroom, blueberry, green coffee berry, green tea, kale, carrot, spinach, lettuce, pumpkin and broccoli.

Furthermore, the medicinal herb layer 22 may be formed by extracting medicinal ingredients from chrysanthemum, lemon, orange, cherry, pomegranate, grape, strawberry rose, lilac, acacia, freesia, lily, lavender, mint, jasmine, mugwort, rosemary, pine, flavonoid, fir, coffee, fingered citron, chamomile, cypress, geranium, juniper, roseclary, sage, lime, neroli, sandalwood bergamot, eucalyptus, lime neroli, peppermint, ylang-ylang, patchouli, myrrh, frankincense, cedarwood or sandalwood and encapsulating them.

Since the above-described medicinal ingredients are naturally occurring antioxidants capable of scavenging activated oxygen reactive oxygen species causing eye fatigue with little toxicity and side effect to the skin, the medicinal ingredients can relieve eye fatigue.

Figure 5:
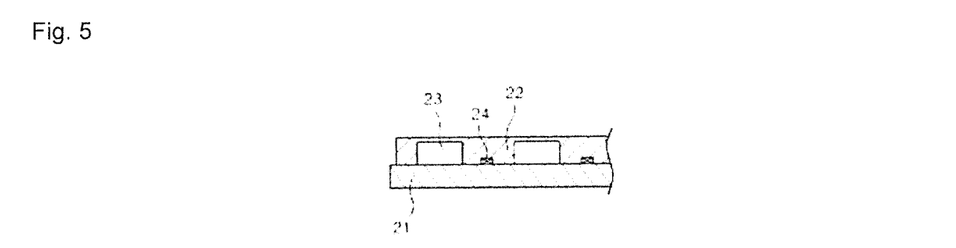
FIG. 5 is a cross-sectional view showing another embodiment wherein a magnet is installed in a drug carrier.

As seen from FIG. 5, a magnet 24 may be further attached to the substrate 21. The magnet 24 generates a magnetic field around the medicinal herb layer 22 and thereby enhances the delivery of the medicinal ingredient. The magnet 24 may be disposed between the light-emitting lamps 23 on the substrate 21, as shown in FIG. 5. Alternatively, a magnet member may be included when preparing the medicinal herb layer 22 containing the medicinal ingredients, so that the medicinal herb layer 22 has magnetic property.

Further, the auxiliary LED light-emitting module 25 is installed on the substrate 21.

The auxiliary LED light-emitting module 25 is mounted on the substrate 21 so as to be positioned below the medicinal herb layer 22 and comprises a plurality of auxiliary LEDs 26 exposed toward the face of the user via the light irradiation holes 16 of the inner case 14.

The auxiliary LEDs 26 irradiate light with wavelength of 430-670 nm. Since light in the wavelength region has skin restoring effect in general, irradiation with the light may reduce wrinkles around the eyes.

However, since the light in the wavelength region may aggravate eye fatigue when irradiated to the eyes, the shielding plates 17 may be equipped as described above to prevent the light emitted from the auxiliary LED light-emitting module 25 from being irradiated to the eyes of the user.

Figure 4:
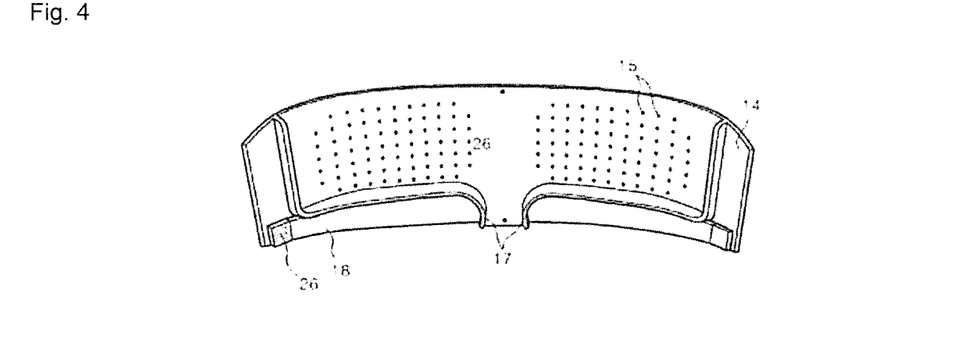
FIG. 4 is a perspective view showing another embodiment wherein a light guide plate is installed at an inner case.

As shown in FIG. 4, a light guide plate 18 may be installed below the shielding plate 17.

In this embodiment, the support worn on the face 1 has only one or two auxiliary LED(s) 26 and the light guide plate 18 irradiates the light emitted from the auxiliary LED(s) 26. In this manner, the number of auxiliary LED(s) 26 to be installed can be reduced and light of uniform intensity may be irradiated on the whole surface.

The fixing member 30 fixes the housing 10 to the face of the user. In this embodiment, the support worn on the face 1 is in the form of glasses, and an end portion of the fixing member 30 is coupled with the housing 10 like the bow of the glasses and extends toward the back of the head of the user.

That is to say, a pair of the fixing members 30 fix the housing 10 while surrounding the user's head at the side.

In this embodiment, the fixing member 30 is made of an elastically deformable material so as to press the user's head from the side. However, the fixing member 30 may also be formed such that the rear end portion is placed over the ear of the user like the bow of the glasses. Alternatively, it may be formed as a belt surrounding the whole head.

The fixing member 30 may also be formed in other different forms as long as it can fix the housing 10 to the face of the user.

The battery 40 is used as a power supply for supplying power to the drug carrier 20, and is installed inside the fixing member 30.

A battery mounting space wherein the battery 40 is mounted is formed in the fixing member 30. Also, a second power supply terminal (not shown) contacting with the first power supply terminal 13 is formed to deliver power from the battery 40. Thus, the power is supplied from the battery 40 to the drug carrier 20.

The battery 40 may be either a rechargeable secondary battery. The battery 40 may be replaced for recharging. Also, a cable port for connection with an external power cable is provided so as to supply power to the drug carrier 20 from an external power supply or recharge the battery 40.

In this embodiment, the battery mounting space is provided in the fixing member 30 to mount the battery 40. Alternatively, the drug carrier may be mounted in the battery mounting space instead of the battery 40, so that the medicinal ingredients are released from the fixing member 30.

The support worn on the face 1 of the present disclosure may be used as follows.

First, the inner case 14 of the housing 10 is fixed by the fixing member 30 so that it is adjacent to the eyes and the face around the eyes.

Then, when power is supplied to the light-emitting lamp 23 and the auxiliary LED 26 by turning on a switch 31, the medicinal ingredients contained in the medicinal herb layer 22 are activated and delivered into the skin through the vent holes 15, while the light irradiated from the auxiliary LED 26 reduces wrinkles around the eyes.

Since the support worn on the face 1 of the present disclosure allows directly transdermal delivery of the medicinal ingredients, it can maximize the eye fatigue relieving effect and, at the same time, can reduce the wrinkles around the eyes.

In the support worn on the face 1 of this embodiment, the outer case 11 is connected to the fixing member 30 and the space of the housing 10 wherein the drug carrier 20 is mounted is opened and closed by the inner case 14. Alternatively, as shown in FIG. 7 and FIG. 8, in a support worn on the face 3 according to a third embodiment, an inner case 81 exposed toward the face of the user may be connected with a fixing member 83, an opening of a mounting space 85 in which a drug carrier 84 is mounted may be formed outside thereof, and a housing 80 may be formed such that an outer case 82 for opening and closing the mounting space 85 is coupled detachably outside the inner case 81.

Figure 7:
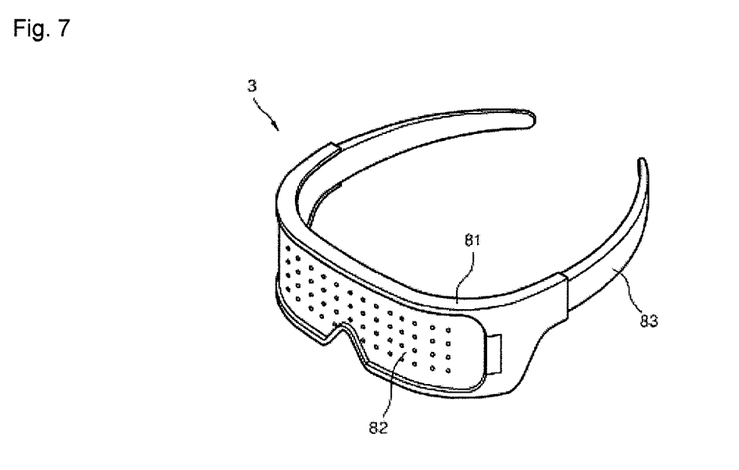
FIG. 7 is a perspective view of a support worn on the face having a built-in drug carrier according to a third embodiment the present disclosure.
Figure 8:
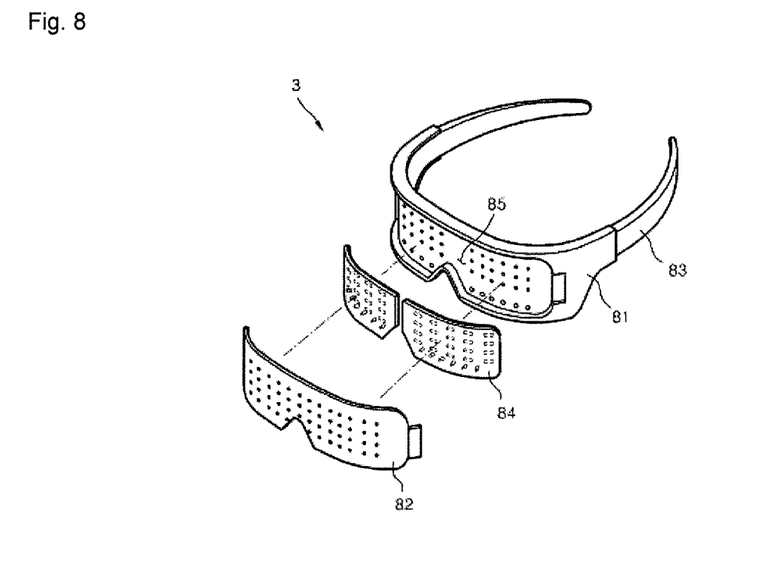
FIG. 8 is an exploded perspective view of FIG. 7.

Detailed description about other elements of the support worn on the face 3 shown in FIG. 7 and FIG. 8 will be omitted since they are identical to those of the foregoing embodiment in configurations and functions.

Figure 6:
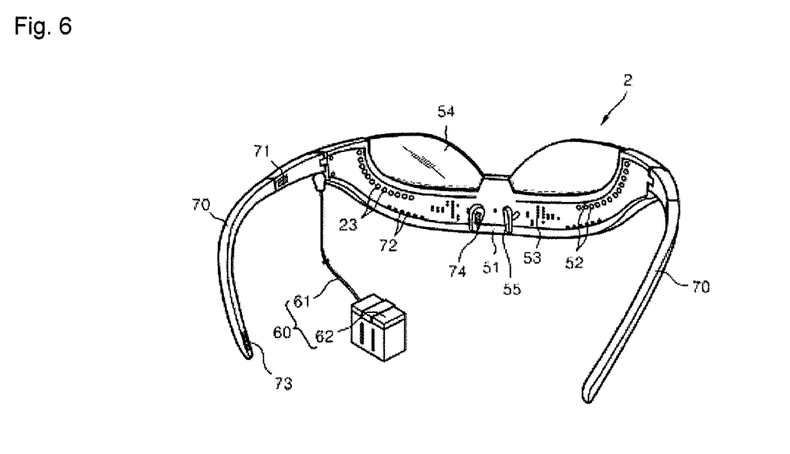
FIG. 6 is a perspective view of a support worn on the face having a built-in drug carrier according to a second embodiment the present disclosure.

FIG. 6 shows a support worn on the face 2 according to a second embodiment of the present disclosure.

Referring to the figure, the support worn on the face 2 of this embodiment has a light transmitting portion 54 formed on one side of a housing 51 so as not to obstruct view when the support worn on the face 2 is worn by the user.

The light transmitting portion 54 comprises a light-transmitting lens such that the view of the user is not obstructed during daily lives such as work or reading when the housing 51 is worn by the user.

The housing 51 surrounding the eyes has a plurality of lamp holes 52 and medicinal ingredient releasing holes 53, which are exposed toward the face.

A drug carrier comprising a light-emitting lamp 23 and a medicinal herb layer is mounted inside the housing 51. Detailed description about the drug carrier will be omitted since it is identical that of the foregoing embodiment in configurations and functions except that it is shaped to correspond to shape of the housing 51.

A power supply 60 for supplying power to the drug carrier comprises a battery 62 that can be worn by the user and an electric cable 61 electrically connecting the battery 62 with the housing 51.

A fixing member 70 extends the housing 51 backwards like the bow of the glasses, and its rear end portion is placed over the ear of the user so as to fix the housing 51 to the face of the user.

A first magnet member 71 generating a magnetic field at the location corresponding to the temple of the user is attached to the fixing member 70.

At the temple is the Taiyang acupoint. In the oriental medicine, it is known that stimulation of the Taiyang acupoint is helpful in relieving fatigue, especially eye fatigue.

Thus, by attaching the first magnet member 71 so as to stimulate the Taiyang acupoint with magnetic field, fatigue relieving effect may be achieved.

Further, a plurality of second magnet members 72 may be installed on the inner surface of the housing 51, so as to stimulate the Qiuhou and Chengqi acupoints located below the globe of the eye with magnetic field. By stimulating these acupoints, the effect of preventing and improving eye diseases such as cataract, glaucoma associated with increased eye pressure, epiphora and conjunctivitis may be achieved.

In addition, a third magnet member 73 is installed at the rear end of the fixing member 70. The rear end of the fixing member 70 is close to the Wangu and Fengchi acupoints at the back of the user's head. Stimulation of these acupoints with magnetic field is effective in preventing or improving diseases such as bradyacusia, insomnia, otitis media, facial edema, headache, cerebral hyperemia, hypertension, ozena, or the like.

Also, nose pads 55 are formed on the housing 51 to contact the ridge of the nose and support the housing 51 when the housing 51 is worn. A fourth magnet member 74 may be installed at the nose pad 55.

The fourth magnet member 74 may generate a magnetic field around the ridge of the nose so as to provide the effect of relieving nose-related diseases such as rhinitis or ozena.

In this embodiment, the first through fourth magnet members 71-74 are installed at the housing 51 and the fixing member 70 so as to stimulate the Taiyang, Qiuhou, Chengqi, Wangu and Fengchi acupoints and the ridge of the nose with magnetic field. However, only some of the first through fourth magnet members 71-74 may be installed, if necessary.

As described above, the support worn on the face 2 of this embodiment is capable of relieving eye fatigue and improving headache, insomnia, etc. by stimulating the acupoints with the magnet members while allowing the release of the medicinal ingredients of the medicinal herb layer 22, without affecting daily lives.

Figure 9:
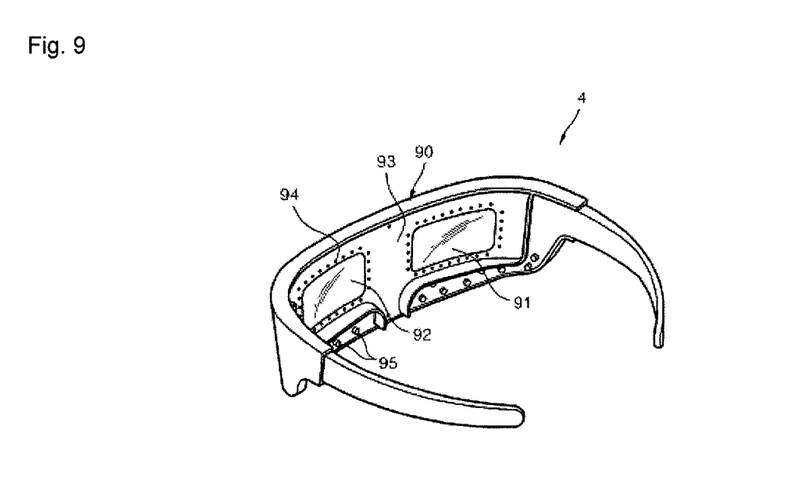
FIG. 9 is a perspective view of a support worn on the face having a built-in drug carrier according to a fourth embodiment the present disclosure.

FIG. 9 shows a support worn on the face 4 according to a fourth embodiment.

Referring to the figure, the support worn on the face 4 of this embodiment has first and second view holes penetrating a housing 90 from front to back. Each of the first and second view holes are formed in front of the right eye and the left eye of the user. And, first and second polarizing lenses 91, 92 are equipped respectively at the first and second view holes.

The first and second polarizing lenses 91, 92 polarize light with different polarizing directions and may be used when watching 3D TV.

Recently, a variety of methods are provided for playback of 3D video images. In this embodiment, the polarizing lenses are used to allow for watching of 3D video. Alternatively, liquid crystal cells may be used instead of the polarizing lenses in order to create 3D images. The medicinal ingredients contained in the drug carrier minimizes eye fatigue during the 3D video watching.

Release holes 94 through which the medicinal ingredients may be released from the drug carrier are formed around the first and second view holes on an inner case 93. And, as in the first embodiment, an auxiliary LED module 95 is provided.

Detailed description about other elements will be omitted since they are identical to those of the foregoing embodiments in configurations and functions.

DETAILED DESCRIPTION OF MAIN ELEMENTS

1: support worn on the face having a built-in drug carrier
2: main body
10: housing
20: drug carrier
30: fixing member
40: battery

The invention claimed is:

1. A support worn on the face having a built-in drug carrier formed to surround the face around the eyes and comprising: a housing with a predetermined installation space defined therein and a plurality of vent holes formed in one side in a proximity of a globe of the eye when the support worn on the face is worn, the vent holes serving to communicate the installation space with an outside; a main body having a fixing member for fixing the housing to the face of a user; a drug carrier installed inside the main body and containing medicinal ingredients useful for protecting the eyes from diseases and relieving eye fatigue; and a power supply supplying power to the drug carrier, wherein the drug carrier comprises a medicinal herb layer containing the medicinal ingredients to enable transdermal delivery of the medicinal ingredients and a substrate supporting the medicinal herb layer and equipped with a light-emitting lamp irradiating IR or UV light to the medicinal herb layer so as to activate the transdermal delivery of the medicinal ingredients contained in the medicinal herb layer.

2. The support worn on the face having a built-in drug carrier of claim 1, wherein the medicinal herb layer comprises a magnet generating a magnetic field or a low frequency generator so as to enhance the transdermal delivery of the medicinal ingredients.

3. The support worn on the face having a built-in drug carrier of claim 1, wherein the housing is equipped with an auxiliary LED light-emitting module irradiating light with wavelength of 430-670 nm toward the face of the user in order to reduce wrinkles around the eyes.

4. The support worn on the face having a built-in drug carrier of claim 1, wherein a light guide plate contacting with the skin around the eyes is formed inside the housing and a light-emitting diode is installed at one side of the light guide plate so as to irradiate light with wavelength of 430-670 nm through the light guide plate.

5. The support worn on the face having a built-in drug carrier of claim 1, wherein the medicinal herb layer comprises a pad formed by pulverizing or extracting at least one medicinal herb selected from duckweed, semiaquilegia, grape, yellow bean, hibisci cortex, citri pericarpium, grape root, lettuce, lettuce seed, pea flower, ginko nut, rugosa rose, sunflower, sunflower root, rose of Sharon, equiseti herba, ginkgonis germen, glycinis testa, ginseng nodus, spinaciae herba, mori cortex, mori fructus, mori folium, persicae fructus immaturus, pruni lignum, pruni resina, pruni radix, pruni folium, pruni ramulus, pruni semen, pruni flos, mori favilla, motherwort, lonicerae folium, lonicerae flos, porpyrae siccus, pruni caulis, persicae calyx, petasiteae rhizoma, colocasiae rhizoma, *Colocasia esculenta* tuber, *Colocasia esculenta* folium, armeniacae semen, ricini semen, glycinis semen ptisanari, whole plant of *Trichosanthes cucumeroides*, pini pollen, fici fructus, brassicae herba, eriobotryae fructus, pini cortex, pini polium, terebinthinae oleum, hirundinis nidus, fucus cum caesalpiniae, fucus cum carthami, *Trichosanthes cucumeroides* semen, melo pediculus, raphani radix, glycine semen nigrae, tuberous root of *Trichosanthes cucumeroides, Trichosanthes cucumeroides* radix, juniperi favilla, ricini folium, carthami flos, carthami novella, trigonellae semen, verbenae herba, carthami semen, curcumae radix, *Curcuma longa* rhizoma, apis nidus, mali fructus, *Angelica sinensis* radix, honey, ginseng, acanthopanacis cortex, hordei fructus germinatus, wild honey, auriculariae polyporus, phragmitis folium, toonae folium, toonae radicis cortex, massa medicata fermentata, phragmitis rhizoma, phragmitis favilla, *Allium fistulosum*, capsellae semen, capsellae herba, coprini herba, *Citrus unshiu* immature peel, *Colocasia esculenta* rhizoma, amaranthi semen, lycii radicis cortex, cyperi rhizoma, perillae folium, allii bulbus, sanguisorbae radix, cnidii rhizoma, *Acorus calamus* rhizoma, papaveris fructus pericarpium, portulacea herba, foeniculi fructus, raphani semen, cnidii surculus, cassiae folium, ixertis herba, lasiosphaera seu calvatia, sacchari tuber, lycii fructus, asparagi radix, liriopes radix, rehmanniae radix, rehmanniae radix preparata, white ginseng, mint, tangerine, sweet potato, poria, dioscoreae rhizoma, achyranthis radix, dendrobii herba, cassiae semen, chrysanthemum, cuscutae semen, aurantii fructus pericarpium, gazellae cornu, saposhnikovia radix, celosiae semen, schizandrae fructus, glycyrrhizae radix, coptidis rhizoma, tribuli fructus, ligustici rhizoma, osterici radix, viticis fructus, glycyrrhizae radix preparata, gypsum, scutellariae radix, forsythiae fructus, moutan cortex, alismatis rhizoma, corni fructus, marigold, angelicae gigantis radix, hirudonis caro, cicadae periostracum, bupleuri radix, cimicifugae rhizoma, clematidis radix, anemarrhenae rhizoma, atractylodis rhizoma, scrophulariae radix, *Angelica pubescens* radix, sophorae radix, thujae resina, *Polygonum multiflorum* radix, astragali radix, schizonepetae spica, fingered citron, banana, mushroom, blueberry, green coffee berry, green tea, kale, carrot, spinach, pumpkin and broccoli.

6. The support worn on the face having a built-in drug carrier of claim 1, wherein the medicinal herb layer comprises at least one medicinal herb selected from lemon, orange, cherry, pomegranate, strawberry, rose, lilac, acacia, freesia, lily, lavender, mint, jasmine, mugwort, rosemary, pine, flavonoid, fir, coffee, fingered citron, chamomile, cypress, geranium, juniper, roseclary, sage, lime, neroli, sandalwood bergamot, eucalyptus, lime neroli, peppermint, ylang-ylang, patchouli, myrrh, frankincense, cedarwood, sandalwood, which is extracted and encapsulated to form the medicinal herb layer.

7. The support worn on the face having a built-in drug carrier of claim 1, wherein the fixing member is formed such that it extends backwards from the housing and its rear ends are placed over the ears of the user, and the housing or the fixing member is equipped with a magnet member capable of stimulating at least one part selected from the Taiyang acupoints corresponding to the temples of the user, the Qiuhou and Chengqi acupoints below the eyes, the Wangu and Fengchi acupoints at the back of the head, and the ridge of the nose.

8. The support worn on the face having a built-in drug carrier of claim 1, wherein view holes are formed in the housing so that the user can see ahead while wearing the support worn on the face.

9. The support worn on the face having a built-in drug carrier of claim 8, wherein a pair of the view holes are formed in the housing, in front of the right and left eyes, and the housing is further equipped with two polarizing lenses of different polarizing directions, each of which is installed to cover each of the view holes.

* * * * *